United States Patent [19]

Stredic, III

[11] Patent Number: 5,738,643
[45] Date of Patent: Apr. 14, 1998

[54] SWAB

[76] Inventor: Prince-Allen Stredic, III, P.O. Box 7047, Austin, Tex. 78713

[21] Appl. No.: 626,518

[22] Filed: Apr. 2, 1996

[51] Int. Cl.$^6$ ............................................. A61M 35/00
[52] U.S. Cl. ............................................. 604/1; 15/210.1
[58] Field of Search ........................... 604/1-3, 294; 15/118, 209.1, 210.1, 214, 220.3; 128/756, 759

[56] References Cited

U.S. PATENT DOCUMENTS

| | | | |
|---|---|---|---|
| D. 49,817 | 10/1916 | Forster . | |
| 1,323,619 | 12/1919 | Curtin . | |
| 1,366,009 | 1/1921 | Lane | 15/210.1 |
| 1,435,890 | 11/1922 | Bothe . | |
| 2,634,497 | 4/1953 | Waldesbuehl . | |
| 2,783,491 | 3/1957 | Bellam | 15/210.1 |
| 2,812,577 | 11/1957 | Leibow . | |
| 4,883,454 | 11/1989 | Hamburg | 604/1 |
| 5,000,202 | 3/1991 | Stepan | 604/1 |
| 5,531,671 | 7/1996 | Bennett | 604/1 |

FOREIGN PATENT DOCUMENTS 447582   7/1927   Germany .

*Primary Examiner*—John G. Weiss
*Assistant Examiner*—Dennis Ruhl
*Attorney, Agent, or Firm*—Stephen R. Greiner

[57] ABSTRACT

An improved swab for surgical and other uses. The swab includes a handle having opposing ends. A cup is secured to one of the opposing ends of the handle. An absorbent material is secured to the cup so as to cover it.

20 Claims, 1 Drawing Sheet

SWAB

FIELD OF THE INVENTION

The present invention relates generally to surgical implements and, in particular, to an improved swab.

BACKGROUND OF THE INVENTION

Conventional swabs, comprising a stick-like handle having a small mass of cotton adhered to one or both of its ends, are in widespread use. For example, such swabs are employed in surgery for wiping bodily tissues and for carrying medicinal liquids thereto. Among other applications, swabs have been used in cleaning delicate machine parts. Conventional swabs, however, are less than satisfactory in collecting and transporting relatively large volumes of solid or liquid material. The present invention overcomes these problems.

SUMMARY OF THE INVENTION

It is a principal object of the invention to provide improved elements and arrangements thereof in a swab which is compact in size, lightweight, inexpensive to manufacture, dependable and fully effective in collecting and transporting relatively large volumes of solid and liquid material.

Briefly, the swab in accordance with this invention achieves its intended object by featuring a handle formed of a resilient plastic material. A small cup is integrally secured to at least one of the opposing ends of the handle. An absorbent cover, comprising unwoven cotton fiber or the like, is adhesively secured to each cup. The absorbent cover acts in the manner of a sponge to soak up and retain material scooped by the cup.

The foregoing and other objects, features and advantages of the present invention will become readily apparent upon further review of the following detailed description of the preferred embodiment as illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENT

Figure 1:
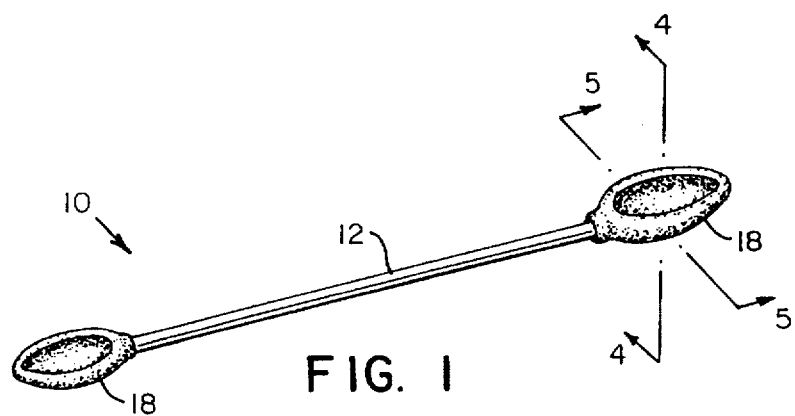
FIG. 1 is a perspective view of a swab in accordance with the present invention.
Figure 2:
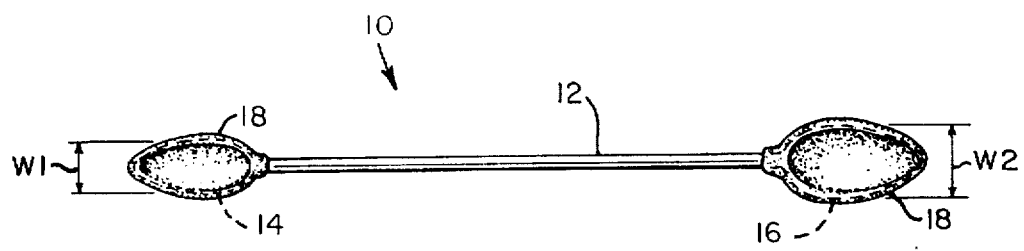
FIG. 2 is a top plan view of the swab.
Figure 3:
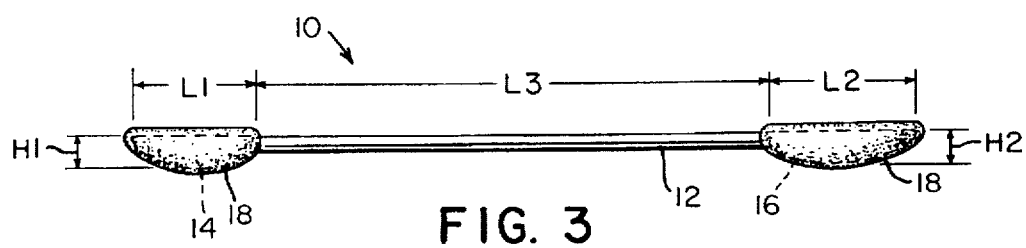
FIG. 3 is a side elevational view thereof.
Figure 4:
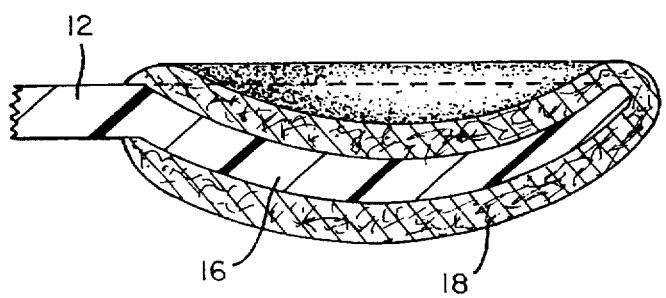
FIG. 4 is a cross-sectional view taken along line 4—4 of FIG. 1.
Figure 5:
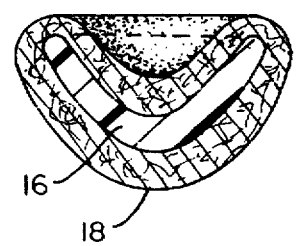
FIG. 5 is a cross-sectional view taken along line 5—5 of FIG. 1.

Referring now to the FIGS., a swab in accordance with the present invention is illustrated generally at 10. The swab 10 includes an elongated, cylindrical handle 12 formed of resilient plastic material. At opposing ends of the handle 12 are integrally secured a pair of cups 14 and 16 having slightly different sizes.

Adhesively secured to each cup 14 and 16 is a cover of absorbent material 18 such as unwoven cotton fiber. The absorbent material 18 fully encloses the cups 14 and 16 so as to prevent such from coming into direct contact with any surface during use. As shown, the handle 12 remains free of absorbent material 18 so that it may be easily grasped within the fingers of a user.

All measurements of the swab 10 are variable depending on the intended use. In the preferred embodiment, however, the handle 12 has a length (L3) of 2.25" (5.715 cm). The cup 14 has a length (L1) of 0.5" (1.27 cm), a width (W1) of 0.25" (0.635 cm) and a height (H1) of 0.125" (0.318 cm). The cup 16, on the other hand, has a length (L2) of 0.625" (1.588 cm), a width (W2) of 0.375" (0.953 cm) and a height (H2) of 0.188" (0.478 cm). The absorbent material 18 forms a layer approximately 0.031" (0.079 cm) thick on both the upper (concave) surface and lower (convex) surface of each cup 14 and 16. Thus, the ends of the preferred swab 10 may be readily inserted into, and withdrawn from, a relatively small opening such as the auditory or nasal cavity of an adult human.

While the invention has been described with a high degree of particularity, it will be appreciated by those skilled in the art that numerous modifications and substitutions may be made thereto. For example, the handle 12 and integral cups 14 and 16 may be formed of any suitable material including: resilient plastic as described above, wood or paperboard. Furthermore, the absorbent material 18 may comprise: cotton, polyester fiber, or porous paper. Therefore, it is to be understood that the present invention is not limited to the sole embodiment described above, but encompasses any and all embodiments within the scope of the following claims.

I claim:

1. A swab, comprising:
    a handle having opposing ends;
    a cup secured to one of said opposing ends of said handle, said cup having a concave upper surface and a convex lower surface; and,
    an absorbent material positioned over and bonded to said concave upper surface and said convex lower surface of said cup.

2. The swab according to claim 1 wherein said handle is formed of a resilient plastic material.

3. The swab according to claim 2 wherein said cup is formed of a resilient plastic material.

4. The swab according to claim 3 wherein said handle and said cup are integrally formed.

5. The swab according to claim 1 wherein said absorbent material fully encloses said cup.

6. The swab according to claim 1 wherein said absorbent material comprises a mass of cotton.

7. A swab, comprising:
    a handle having opposing ends;
    a cup formed with an upstanding peripheral rim, said rim being integrally secured to one of said opposing ends of said handle; and, an absorbent material covering said cup adjacent said handle.

8. The swab according to claim 7 wherein said handle and said cup are formed of a resilient plastic material.

9. The swab according to claim 8 wherein said absorbent material comprises a mass of cotton.

10. A swab, comprising:
    an elongated handle having opposing ends;
    a pair of cups each being formed with an upstanding peripheral rim, each said rim being respectively secured to one of said opposing ends of said handle; and,
    an absorbent material positioned over and adhesively secured to each said cup.

11. The swab according to claim 10 wherein said elongated handle and each said cup are integrally formed from a resilient plastic material.

12. The swab according to claim 11 wherein said absorbent material comprises a mass of unwoven cotton.

13. The swab according to claim 11 wherein said absorbent material comprises polyester fiber.

14. The swab according to claim 11 wherein said absorbent material comprises absorbent paper.

15. The swab according to claim 1 wherein said cup is oval-shaped.

16. The swab according to claim 7 wherein said cup has a concave upper surface and a convex lower surface and said absorbent material is positioned over and bonded to said concave upper surface and said convex lower surface.

17. The swab according to claim 7 wherein said rim of said cup is an oval.

18. The swab according to claim 10 wherein each of said cups has a concave upper surface and a convex lower surface and said absorbent material is positioned over and bonded to said concave upper surface and said convex lower surface of each said cup.

19. The swab according to claim 10 wherein said rim of each said cup is an oval.

20. The swab according to claim 10 wherein the length of one of said cups is larger than the length of the other one of said cups.

* * * * *